(12) United States Patent
Sunderland

(10) Patent No.: US 8,128,869 B2
(45) Date of Patent: Mar. 6, 2012

(54) AIR SANITIZATION SYSTEM WITH VARIABLE SPEED FAN

(75) Inventor: Ted Wayne Sunderland, Troy, MO (US)

(73) Assignee: Hussmann Corporation, Bridgeton, MO (US)

(*) Notice: Subject to any disclaimer, the term of this patent is extended or adjusted under 35 U.S.C. 154(b) by 366 days.

(21) Appl. No.: 12/573,240

(22) Filed: Oct. 5, 2009

(65) Prior Publication Data

US 2011/0081273 A1  Apr. 7, 2011

(51) Int. Cl.
| | |
|---|---|
| A61L 9/00 | (2006.01) |
| A61L 2/00 | (2006.01) |
| B01J 19/08 | (2006.01) |
| B09B 3/00 | (2006.01) |
| G01N 19/10 | (2006.01) |
| B08B 3/12 | (2006.01) |
| B03C 3/36 | (2006.01) |
| B01D 46/30 | (2006.01) |
| B03C 3/00 | (2006.01) |
| F24F 7/007 | (2006.01) |
| H01T 19/04 | (2006.01) |
| A61N 5/00 | (2006.01) |

(52) U.S. Cl. ......... 422/22; 422/1; 422/3; 422/5; 422/24; 422/107; 422/108; 422/119; 422/121; 422/124; 422/186.04; 422/186.3; 422/305; 422/306; 73/23.2; 95/3; 95/25; 95/57; 96/15; 96/54; 96/224; 96/397; 454/228; 588/301; 588/900; 134/1; 250/325; 250/423 R; 250/432 R; 250/492.1

(58) Field of Classification Search .............. 422/1, 3, 422/5, 22, 24, 107–108, 119, 121, 124, 186.04, 422/186.07, 186.3, 305–306; 73/23.2; 95/3, 95/25, 57; 96/15, 54, 224, 397; 454/228; 588/301, 900; 134/1; 250/325, 423 R, 432 R, 250/492.1

See application file for complete search history.

(56) References Cited

U.S. PATENT DOCUMENTS

| | | | |
|---|---|---|---|
| 4,253,852 A | 3/1981 | Adams | |
| 5,946,919 A | 9/1999 | McKinney et al. | |
| 5,997,619 A | 12/1999 | Knuth et al. | |
| 6,558,640 B1 | 5/2003 | Nottingham et al. | |
| 6,656,434 B1 | 12/2003 | Demarcki | |
| 6,716,406 B2 | 4/2004 | Reisfeld et al. | |
| 6,787,104 B1 * | 9/2004 | Mariella, Jr. | 422/4 |
| 2003/0044308 A1 | 3/2003 | Toth | |
| 2006/0034737 A1 | 2/2006 | Beam et al. | |
| 2007/0013910 A1 | 1/2007 | Jiang et al. | |
| 2007/0154344 A1 | 7/2007 | Choi et al. | |
| 2008/0175761 A1 | 7/2008 | Thur et al. | |

FOREIGN PATENT DOCUMENTS

KR   1020050088156   9/2005

* cited by examiner

*Primary Examiner* — Jill Warden
*Assistant Examiner* — Monzer Chorbaji
(74) *Attorney, Agent, or Firm* — Michael Best & Friedrich LLP

(57) ABSTRACT

An air sanitization system including a reactive oxygen species generator, a variable speed fan, a pathogen sensor and a controller. The reactive oxygen species generator generates reactive oxygen species from an oxygen-containing gas and discharges the reactive oxygen species to a conditioned space. The variable speed fan directs the oxygen-containing gas to the reactive oxygen species generator at a controlled speed. The pathogen sensor senses a level of airborne pathogens in the conditioned space and generates a signal indicative of the level of pathogens sensed. The controller receives the signal from the pathogen sensor and varies the speed of the variable speed fan in response to the signal to decrease a speed of the variable speed fan in response to an increase in the level of airborne pathogens sensed by the pathogen sensor.

20 Claims, 2 Drawing Sheets

AIR SANITIZATION SYSTEM WITH VARIABLE SPEED FAN

BACKGROUND

The present invention relates to an air sanitization system generating ozone and other reactive oxygen species, and a control system therefor.

U.S. Patent Publication No. 2007/0154344 discloses a sterilizer unit that produces ozone for killing mold and viruses in an interior space. The temperature and relative humidity of the interior space are measured by sensors and are indicative of the favorability of growing conditions for the mold and viruses. A control unit determines a mode of operation based on the sensed temperature and relative humidity. For more favorable mold and virus growing conditions, the control unit increases ozone production and increases a speed of a blower unit to the ozone generator.

SUMMARY

In one embodiment, the invention provides an air sanitization system including a reactive oxygen species generator, a variable speed fan, a pathogen sensor and a controller. The reactive oxygen species generator generates reactive oxygen species from an oxygen-containing gas and discharges the reactive oxygen species to a conditioned space. The variable speed fan directs the oxygen-containing gas to the reactive oxygen species generator at a controlled speed. The pathogen sensor senses a level of airborne pathogens in the conditioned space and generates a signal indicative of the level of pathogens sensed. The controller receives the signal from the pathogen sensor and varies the speed of the variable speed fan in response to the signal to decrease a speed of the variable speed fan in response to an increase in the level of airborne pathogens sensed by the pathogen sensor.

In another embodiment, the invention provides a method of controlling an air sanitization system for sanitizing a conditioned space. The method includes generating short-lived reactive oxygen species in the reaction chamber, generating long-lived reactive oxygen species in the reaction chamber, passing a pathogen-containing gas through the reaction chamber to remove at least a portion of pathogens from the pathogen-containing gas, distributing the long-lived reactive oxygen species to the conditioned space and onto surfaces in the conditioned space, sensing an amount of pathogens in the pathogen-containing gas, increasing a dwell time of a portion of the pathogen-containing gas within the reaction chamber in response to an increase in the amount of pathogens sensed to increase exposure of the pathogens to the short-lived reactive oxygen species, and decreasing the dwell time of a portion of the pathogen-containing gas within the reaction chamber in response to a decrease in the amount of pathogens to increase distribution of long-lived reactive oxygen species to the conditioned space for sanitizing the surfaces.

In yet another embodiment, the invention provides an air sanitization system. The air sanitization system includes a reactive oxygen species generator, a variable speed fan, a pathogen sensor, and a controller. The reactive oxygen species generator generates reactive oxygen species from an oxygen-containing gas and discharges the reactive oxygen species to a conditioned space. The variable speed fan directs the oxygen-containing gas to the reactive oxygen species generator at a controlled speed. The pathogen sensor senses a level of airborne pathogens in the conditioned space and generates a signal indicative of the level of pathogens sensed. The controller receives the signal from the pathogen sensor and varies the speed of the variable speed fan in response to the signal to decrease a speed of the variable speed fan in response to an increase in the level of airborne pathogens sensed by the pathogen sensor and to increase the speed of the variable speed fan in response to a decrease in the level of airborne pathogens sensed by the pathogen sensor. The controller decreases the fan speed by a predetermined percentage when the level of airborne pathogens is greater than or equal to a predetermined maximum level of airborne pathogens. The controller increases the fan speed by another predetermined percentage when the pathogen level is less than or equal to a predetermined minimum level of airborne pathogens. The reactive oxygen species include at least ozone and vapor phase hydrogen peroxide, and the ozone and vapor phase hydrogen peroxide are delivered to the conditioned space to provide surface and air decontamination.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Figure 1:
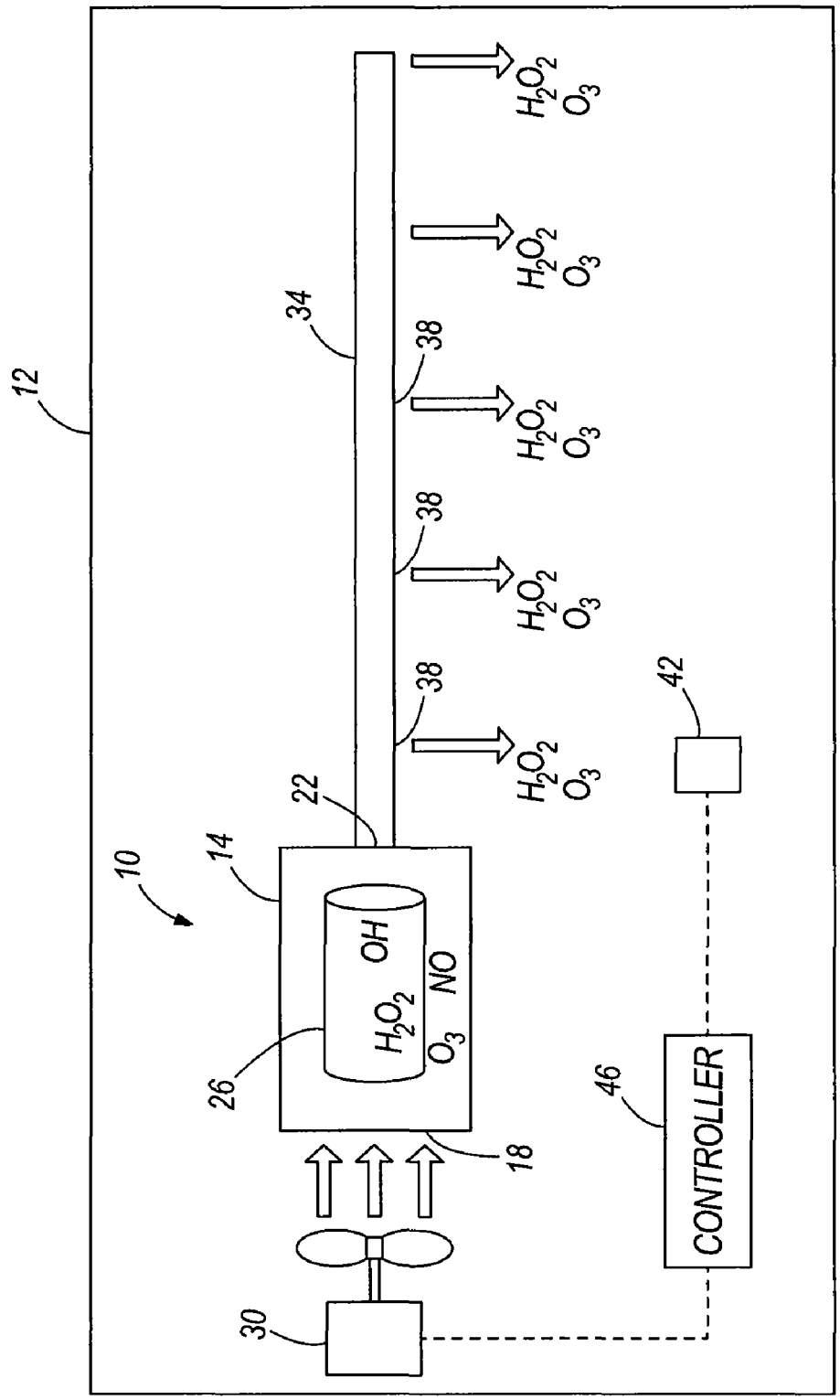
FIG. 1 is a schematic diagram of an air sanitization system in accordance with the present invention.

FIG. 1 illustrates an air sanitization system 10 for sanitizing air and surfaces of a conditioned space 12. The air sanitization system 10 has a reaction chamber 14 having an inlet 18 and an outlet 22, a reactive oxygen species (ROS) generator 26 housed within the reaction chamber 14 and positioned between the inlet 18 and outlet 22, and a variable speed fan 30 positioned to deliver a variable speed flow of pathogen- and oxygen-containing gas to the inlet 18 of the reaction chamber 14. The outlet 22 is coupled to a diffuser 34 for distributing cleaned air and reactive oxygen species to the conditioned space 12.

The ROS generator 26 preferably includes a dielectric barrier discharge (DBD) plasma generator, such as the ROS generator described in U.S. Patent Application Publication No. 2007/0119699, filed Nov. 30, 2005, which is incorporated by reference herein. The ROS generator 26 generates reactive oxygen species from an oxygen-containing gas. Reactive oxygen species oxidize pollutants to effectively remove them from the air and surfaces. Reactive oxygen species include one or more of oxygen ions, free radicals, organic and inorganic peroxides, ozone, and other reactive oxygen species, some of which are long-lived and some of which are short-lived. For example, hydroxide and nitric oxide are short-lived reactive oxygen species, and vapor phase hydrogen peroxide and ozone are long-lived reactive oxygen species. The long-lived ROS survive to be distributed into the conditioned space 12, while the short-lived ROS are active substantially within the reaction chamber 14. In other constructions, other types of ROS generators may be employed.

The variable speed fan 30 is positioned adjacent the inlet 18 of the reaction chamber 14 and delivers a flow of pathogen- and oxygen-containing gas from the conditioned space 12 to the ROS generator 26 to be converted into reactive oxygen species and cleaned. The fan 30 is operable at multiple speeds and is preferably operable at one- or five-percent increments of speed between zero and 100% full speed. In other constructions, the variable speed fan 30 may be positioned elsewhere upstream or downstream of the ROS generator 26 to direct gas to the ROS generator 26, and other types of variable speed fans capable of being controlled to operate at multiple speeds may also be employed.

The diffuser 34 is coupled to the outlet 22 of the reaction chamber 14 for directing an output gas from the reaction chamber 14 into the conditioned space 12. The output gas includes cleaned air and reactive oxygen species containing primarily long-lived ROS generated by the ROS generator 26. The diffuser 34 includes multiple outlets 38 for distributing the output gas to various locations within the conditioned space 12, preferably for even, or nearly even, distribution. In other constructions, the distribution of the output gas can be distributed unevenly by the diffuser. In yet other constructions, other types of diffusers may be employed, and in other constructions still, no diffuser may be employed.

A pathogen sensor 42 is positioned in the conditioned space 12 for sensing a level of pathogens in the conditioned space 12, and more particularly, the level of airborne pathogens in the conditioned space 12. Pathogens include, but are not limited to, bacteria, viruses, mold and fungi. The pathogen sensor 42 is preferably an electrochemical sensor chip for rapid pathogen detection and generation of an electrical signal indicative of a level of pathogens sensed. Several rapid response pathogen sensing technologies currently exist and are suitable for use with the present invention. In other constructions, other types of pathogen sensors may be employed.

The pathogen sensor 42 is operatively coupled to a controller 46 for supplying an electrical signal to the controller 46 indicative of the level of pathogens in the conditioned space 12. The controller 46 is operatively coupled to the variable speed fan 30 for controlling the speed of the fan 30 dependent on the level of pathogens sensed by the pathogen sensor 42. The controller 46 is operable to decrease the speed of the variable speed fan 30 in response to an increase in the level of airborne pathogens sensed by the pathogen sensor 42. Conversely, the controller 46 is operable to increase the speed of the variable speed fan 30 in response to a decrease in the level of airborne pathogens sensed by the pathogen sensor 42. Decreasing the speed of the variable speed fan 30 increases a dwell time of a volume of air within the reaction chamber 14. Conversely, increasing the speed of the variable speed fan 30 decreases the dwell time of a volume of air within the reaction chamber 14.

The generation of ROS decreases when the fan 30 is slowed because less oxygen is introduced to the generator 26 for conversion into ROS. However, the short-lived ROS, which are active substantially within the reaction chamber 14, are able to find and neutralize more pathogens when pathogens dwell longer within the reaction chamber 14. Thus, when the fan speed is decreased, more airborne pathogens are neutralized within the reaction chamber 14. Conversely, the generation of ROS increases when the speed of the fan 30 is increased because more oxygen is converted to ROS. When the fan speed is increased, more long-lived ROS are released to the conditioned space 12 for increased surface sanitization in the conditioned space. Thus, maximum benefit of the air sanitization system 10 is achieved in both pathogen removal from the room atmosphere (i.e., the conditioned space 12) as well as surface sanitization within the conditioned space 12 by decreasing the fan speed with increasing pathogen level, and increasing the fan speed with decreasing pathogen level.

Figure 2:
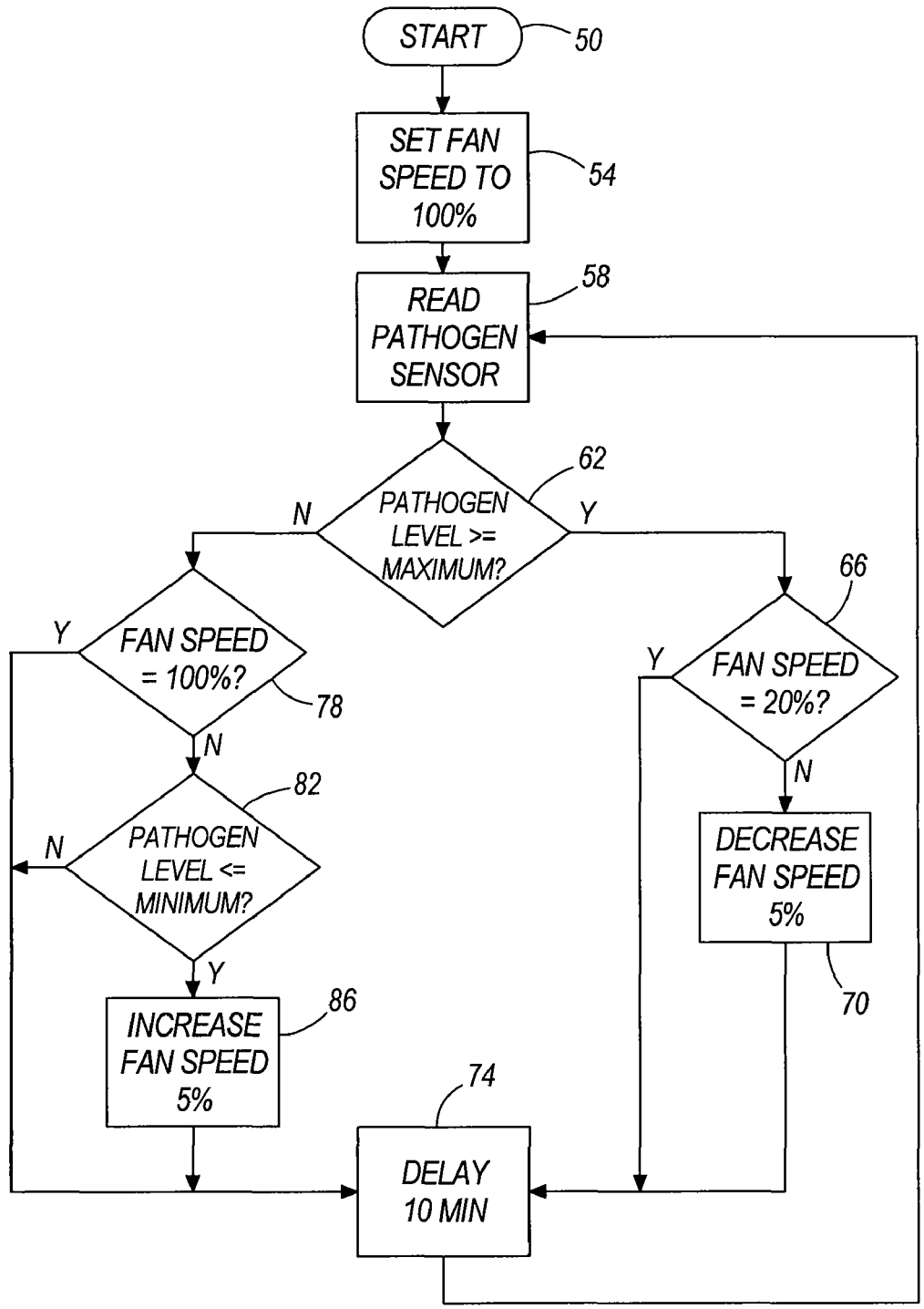
FIG. 2 is a flow chart of an algorithm for controlling the air sanitization system of FIG. 1.

FIG. 2 illustrates an algorithm for controlling the air sanitization system 10. At action 50, the algorithm starts and moves to action 54. At action 54, the controller 46 sets the speed of the fan 30 to 100% (full speed), and moves to action 58. At action 58, the controller 46 reads a signal from the pathogen sensor 42 corresponding to a pathogen level, and moves to action 62. At action 62, the controller 46 determines whether the pathogen level is greater than or equal to a maximum pathogen level, which is a predetermined level at which more pathogen removal within the reaction chamber 14 is desired. If the pathogen level is greater than or equal to the maximum, the controller 46 moves to action 66 to determine whether the speed of the fan 30 is equal to twenty percent. If the speed is not equal to twenty percent, the controller 46 moves to action 70 and decreases the fan speed by five percent, and then moves to action 74 to a ten minute delay before returning to action 58. If the speed is equal to twenty percent, the controller 46 moves directly to action 74 for a ten minute delay before returning to action 58.

If, at action 62, the pathogen level is not greater than or equal to the maximum, the controller moves to action 78 to determine whether the fan speed is equal to 100% (full speed). If the fan speed is not equal to 100%, the controller moves to action 82 to determine whether the pathogen level is less than or equal to a minimum pathogen level, which is a predetermined level at which more surface sanitization is desired. If the pathogen level is less than or equal to the minimum, the controller 46 moves to action 86 to increase the speed of the fan 30 by five percent, and then moves to action 74 to a ten minute delay before returning to action 58. If the pathogen level is not less than nor equal to the minimum, the controller 46 moves to action 74 for a ten minute delay before returning to action 58.

In operation, the ROS generator 26 generates short- and long-lived ROS for cleaning the air and surfaces of the conditioned space 12. The controller 46 decreases the speed of the fan 30 in five percent increments when the pathogen level is over the maximum pathogen level, but does not decrease the speed below twenty percent. Decreasing the fan speed increases the dwell time of the pathogen-containing air in the reaction chamber 14, which increases the effectiveness of the short-lived ROS. If the pathogen level is below the minimum level, the controller 46 increases the speed of the fan 30 in five percent increments. At higher fan speeds, more long-lived ROS are delivered to the conditioned space 12 for surface and air sanitization. Regardless of the fan speed, cleaned air and ROS are delivered from the reaction chamber 14 to the conditioned space 12 by way of the diffuser 34, which distributes the air and ROS throughout the conditioned space.

In another construction, the controller 46 includes a user input feature. For example, a user may select one of maximum air sanitization and maximum surface decontamination. When maximum air sanitization is selected, the controller 46 decreases the fan speed. For example, the fan speed may be decreased to twenty percent. When maximum surface decontamination is selected, the controller 46 increases the fan speed. For example, the fan speed may be increased to full speed. The user input feature may be added to the air sanitization system 10 of FIGS. 1-2, or may be a feature of a different air sanitization system.

Thus, the invention provides, among other things, a control system for an air sanitization system and a method of operating the air sanitization system. Various features and advantages of the invention are set forth in the following claims.

What is claimed is:

1. An air sanitization system, comprising:
a reactive oxygen species generator for generating reactive oxygen species from an oxygen-containing gas and for discharging the reactive oxygen species to a conditioned space;
a variable speed fan for directing the oxygen-containing gas to the reactive oxygen species generator at a controlled speed;
a pathogen sensor for sensing a level of airborne pathogens in the conditioned space and for generating a signal indicative of the level of pathogens sensed; and
a controller for receiving the signal from the pathogen sensor, the controller varying the speed of the variable speed fan in response to the signal to decrease a speed of the variable speed fan in response to an increase in the level of airborne pathogens sensed by the pathogen sensor.

2. The air sanitization of claim 1, wherein the controller is operable to increase the speed of the variable speed fan in response to a decrease in the level of airborne pathogens sensed by the pathogen sensor.

3. The air sanitization of claim 1, wherein the reactive oxygen species generator is a dielectric barrier discharge plasma generator.

4. The air sanitization of claim 1, wherein the reactive oxygen species include at least ozone and vapor phase hydrogen peroxide, and wherein the ozone and vapor phase hydrogen peroxide are delivered to the conditioned space to provide surface and air decontamination.

5. The air sanitization of claim 4, further comprising a diffusion apparatus attached to an outlet of the reactive oxygen species generator, wherein the diffusion apparatus distributes the reactive oxygen species to the conditioned space.

6. The air sanitization of claim 1, wherein the controller further comprises a user input receiving function including a maximum air sanitization option and a maximum surface decontamination option, wherein the controller decreases the fan speed when the maximum air sanitization option is selected and increases the fan speed when the maximum surface decontamination option is selected.

7. The air sanitization of claim 1, wherein the controller decreases the fan speed by a predetermined percentage when the level of airborne pathogens is greater than or equal to a predetermined maximum level of airborne pathogens.

8. The air sanitization of claim 7, wherein the controller increases the fan speed by another predetermined percentage when the pathogen level is less than or equal to a predetermined minimum level of airborne pathogens.

9. The air sanitization of claim 8, wherein the controller delays a reading of the pathogen sensor by a predetermined time period each time the fan speed is changed.

10. A method of controlling an air sanitization system for sanitizing a conditioned space, the method comprising:
generating short-lived reactive oxygen species in the reaction chamber;
generating long-lived reactive oxygen species in the reaction chamber;
passing a pathogen-containing gas through the reaction chamber to remove at least a portion of pathogens from the pathogen-containing gas;
distributing the long-lived reactive oxygen species to the conditioned space and onto surfaces in the conditioned space;
sensing an amount of pathogens in the pathogen-containing gas;
increasing a dwell time of a portion of the pathogen-containing gas within the reaction chamber in response to an increase in the amount of pathogens sensed to increase exposure of the pathogens to the short-lived reactive oxygen species; and
decreasing the dwell time of a portion of the pathogen-containing gas within the reaction chamber in response to a decrease in the amount of pathogens to increase distribution of long-lived reactive oxygen species to the conditioned space for sanitizing the surfaces.

11. The method of claim 10, wherein generating long-lived reactive oxygen species includes generating at least one of ozone and vapor phase hydrogen peroxide.

12. The method of claim 11, wherein generating short-lived reactive oxygen species includes generating at least one of hydroxide and nitric oxide.

13. The method of claim 10, wherein increasing the dwell time includes decreasing a fan speed to decrease an amount of gas passing through the reaction chamber.

14. The method of claim 13, wherein decreasing the dwell time includes increasing the fan speed to increase the amount of gas passing through the reaction chamber.

15. The method of claim 14, wherein increasing the dwell time includes decreasing the fan speed in increments of a first predetermined percentage, and decreasing the dwell time includes increasing the fan speed in increments of a second predetermined percentage.

16. The method of claim 15, further comprising waiting a predetermined time period between increasing or decreasing the fan speed and sensing the amount of pathogens in the pathogen-containing gas.

17. The method of claim 13, wherein increasing the dwell time includes decreasing the fan speed in increments of a predetermined percentage.

18. The method of claim 10, wherein distributing the long-lived reactive oxygen species includes directing the long-lived reactive oxygen species from an outlet of the reaction chamber to a diffuser.

19. The method of claim 10, further comprising:
increasing the dwell time of a portion of air within the reaction chamber in response to a user input requesting air sanitization; and
decreasing the dwell time of a portion of air within the reaction chamber in response to a user input requesting surface decontamination in the conditioned space.

20. An air sanitization system, comprising:
a reactive oxygen species generator for generating reactive oxygen species from an oxygen-containing gas and for discharging the reactive oxygen species to a conditioned space;
a variable speed fan for directing the oxygen-containing gas to the reactive oxygen species generator at a controlled speed;
a pathogen sensor for sensing a level of airborne pathogens in the conditioned space and for generating a signal indicative of the level of pathogens sensed; and a controller for receiving the signal from the pathogen sensor, the controller varying the speed of the variable speed fan in response to the signal to decrease a speed of the variable speed fan in response to an increase in the level of airborne pathogens sensed by the pathogen sensor and increase the speed of the variable speed fan in response to a decrease in the level of airborne pathogens sensed by the pathogen sensor;

wherein the controller decreases the fan speed by a predetermined percentage when the level of airborne pathogens is greater than or equal to a predetermined maximum level of airborne pathogens;

wherein the controller increases the fan speed by another predetermined percentage when the pathogen level is less than or equal to a predetermined minimum level of airborne pathogens; and wherein the reactive oxygen species include at least ozone and vapor phase hydrogen peroxide, and wherein the ozone and vapor phase hydrogen peroxide are delivered to the conditioned space to provide surface and air decontamination.

* * * * *